US009554578B2

(12) United States Patent
Royalty et al.

(10) Patent No.: US 9,554,578 B2
(45) Date of Patent: Jan. 31, 2017

(54) BIOCONTROL OF NEMATODES

(75) Inventors: Reed Nathan Royalty, Davis, CA (US); Varghese Thomas, Davis, CA (US); Roy Whitson, Fresno, CA (US)

(73) Assignee: Bayer CropScience LP, Research Triangle Park, NC (US)

( * ) Notice: Subject to any disclaimer, the term of this patent is extended or adjusted under 35 U.S.C. 154(b) by 5 days.

(21) Appl. No.: 13/556,613

(22) Filed: Jul. 24, 2012

(65) Prior Publication Data

US 2013/0189227 A1 Jul. 25, 2013

Related U.S. Application Data

(60) Provisional application No. 61/511,508, filed on Jul. 25, 2011, provisional application No. 61/556,016, filed on Nov. 4, 2011, provisional application No. 61/661,763, filed on Jun. 19, 2012.

(51) Int. Cl.
*A01N 63/00* (2006.01)
(52) U.S. Cl.
CPC ...................................... *A01N 63/00* (2013.01)
(58) Field of Classification Search
USPC .......................................................... 514/341
See application file for complete search history.

(56) References Cited

U.S. PATENT DOCUMENTS

| | | | |
|---|---|---|---|
| 6,015,553 A | 1/2000 | Germida et al. | |
| 6,060,051 A | 5/2000 | Heins et al. | |
| 6,103,228 A | 8/2000 | Heins et al. | |
| 6,291,426 B1 | 9/2001 | Heins et al. | |
| 6,417,163 B1 | 7/2002 | Heins et al. | |
| 6,524,998 B1 | 2/2003 | Kloepper et al. | |
| 6,638,910 B2 | 10/2003 | Heins et al. | |
| 6,896,883 B2 * | 5/2005 | Bergstrom et al. | 424/93.462 |
| 2010/0064393 A1 | 3/2010 | Berka et al. | |
| 2011/0154544 A1 | 6/2011 | Riggs | |
| 2014/0005047 A1 | 1/2014 | Hungenberg et al. | |

FOREIGN PATENT DOCUMENTS

| | | |
|---|---|---|
| EP | 2460407 A1 | 6/2012 |
| WO | WO 00/38510 A1 | 7/2000 |
| WO | WO 00/42855 A1 | 7/2000 |
| WO | WO 2007/104570 A2 | 9/2007 |
| WO | WO 2008/152589 A2 | 12/2008 |
| WO | WO2010030554 A1 | 3/2010 |
| WO | WO2010128003 A2 | 11/2010 |
| WO | WO2012087980 A1 | 6/2012 |

OTHER PUBLICATIONS

AgraQuest "Senerade® Max product sheet", available online Sep. 10, 2010.*
Choudhary, D. K., et al., "Interactions of *Bacillus* spp. and plants—With special reference to induced systemic resistance (ISR)," Microbiological Research, vol. 64, No. 5, pp. 493-513, Sep. 29, 2009.
Merckling, T., et al., "AgraQuest: Development of Serenade as a biopesticide against plant bacterial diseases," Annual COST873 Meeting—Management Committee Meeting, 35 pages, Oct. 26, 2009.
Niknam, G. R., et al., "Induction of Systemic Resistance by Bacillus subtilis Isolate Bst Against Rotylenchulus Reniformis in Tomato," Nematologia Mediterranea, vol. 31, No. 2, pp. 239-243, Jan. 1, 2003.
International Search Report & Written Opinion of the International Searching Authority, PCT/US2012/047963, dated Nov. 23, 2012, 13 pages.
Dawar, S., et al., "Application of *Bacillus* Species in Control of Meloidogyne javanica (Treub) Chitwood on Cowpea and Mash Bean", Pak. J. Bot., 2008, 40:439-444.
Kokalis-Burelle, N., et al., "Field Evaluation of Plant Growth-Promoting Rhizobacteria Amended Transplant Mixes and Soil Solarization for Tomato and Pepper Production in Florida", Plant and Soil, 2002, 238:257-266.
Lian, L.H., et al., "Proteases from Bacillus: A New Insight into the Mechanism of Action for Rhizobacterial Suppression of Nematode Populations", Letters of Applied Microbiology, 2007, 45:262-269.
Lobna, M. & Zawam, H., "Efficacy of some Biocontrol Agents on Reproduction and Development of Meloidogyne incognita Infecting Tomato", Journal of American Science, 2010, 6:495-509.
Siddiqui, Z.A. & Akhtar, M.S., "Effects of Antagonistic Fungi, Plant Growth-Promoting Rhizobacteria, and Arbuscular Mycorrhizal Fungi Alone and in Combination on the Reproduction of Meloidogyne incognita and Growth of Tomato", J. Gen. Plant Pathol., 2009, 75:144-153.
Tariq, M. & Dawar, S., "Impact of Biocontrol Bacteria with Rhizophora mucronata Plant Parts in Suppression of Meloidogyne javanica (treub) Chitwood on Crop Plants", Archives of Phytopathology and Plant Protection, 2010, 43:754-760.
Tian, B., et al., "Bacteria Used in the Biological Control of Plant-Parasitic Nematodes: Populations, Mechanisms of Action, and Future Prospects", FEMS Microbiol. Ecol., 2007, 61:197-213.

(Continued)

*Primary Examiner* — Emily Cordas
(74) *Attorney, Agent, or Firm* — Adam L. Lunceford; Michelle L. Samonek

(57) ABSTRACT

The present invention provides a method for using a *Bacillus* strain as a nematicide and related compositions.

18 Claims, 11 Drawing Sheets

(56) References Cited

OTHER PUBLICATIONS

Bais, et al., "Biocontrol of Bacillus subtilis Against Infection of Arabidopsis Roots by Pseudomonas syringae is Facilitated by Biofilm Formation and Surfactin Production," Plant Physiol. (2004) 134:307-319.
Branda, et al., "Fruiting Body Formation by Bacillus subtilis," Proc. Natl. Acad. Sci. USA (2001) 98:11621-11626.
Calvio, et al., "Autoregulation of swrAA and Motility in Bacillus subtilis," Journal of Bacteriology (2008) 190:5720-5728.
Calvio et al., "Swarming Differentiation and Swimming Motility in Bacillus subtilis Are Controlled by swrA, a Newly Identified Dicistronic Operon," Journal of Bacteriology (2005) 187(15):5356-5366.
Chen et al., "Comparative analysis of the complete genome sequence of the plant growth-promoting bacterium Bacillus amyloliquefaciens FZB42," Nature Biotechnology (2007) 25(9):1007-1014.
Kearns et al., "Cell Population Heterogeneity During Growth of Bacillus subtilis," Genes & Development (2005) 19:3083-3094.
Kearns, et al., "Genes Governing Swarming in Bacillus subtilis and Evidence for a Phase Variation Mechanism Controlling Surface Motility," Molecular Microbiology (2004) 52(2):357-369.
Kloeper et al., "Induced systemic resistance and promotion of plant growth by *Bacillus* spp.," Phytopathology (2004) 94(11):1259-1266.
Lemon, et al., "Biofilm Development with an Emphasis on Bacillus subtilis," (2008) Current Topics in Microbiology and Immunology (2008) 322:1-16.
McLoon, A., et al., "Tracing the Domestication of a Biofilm-Forming Bacterium" Journal of Bacteriology, Apr. 2011 2027-2034.
Merckling, T., et al., "Development of Serenade as a Biopesticide Against Plant Bacterial Diseases," Annual COST873 Meeting—Management Committee Meeting, Oct. 26, 2009, pp. 1-35.
Morikawa, "Beneficial biofilm formation by industrial bacteria Bacillus subtilis and Related Species," Journal of Bioscience and Bioengineering (2006) 101(1):1-8.
Osera et al., "SwrAA Activates Poly-3•-glutamate Synthesis in Addition to Swarming in Bacillus subtilis," Microbiology (2009) 155, 2282-2287.
Patrick, J.E. and Kearns, D.B., "Laboratory Strains of Bacillus subtilis Do Not Exhibit Swarming Motility," Journal of Bacteriology (2009) 191(22): 7129-7133.
Rudrappa et al., "Causes and Consequences of Plant-Associated Biofilms," FEMS Microbiology Ecology (2008) 64:153-166.
Stanley, N. and Lazazzera, B., "Defining the Genetic Differences Between Wild and Domestic Strains of Bacillus subtilis that Affect Poly-•-DL-Glutamic Acid Production and Biofilm Formation," Molecular Microbiology (2005) 57(4):1143-1158.
"Review Report for the Active Substance Bacillus subtilis QST713", Jul. 14, 2006, pp. 1-24, Retrieved from the Internet: URL:http://ec.europa.eu/food/plant/protection/evaluation/newactive/bacillus_subtilis_report_final.pdf.
International Search Report and Written Opinion of the International Searching Authority, International Patent Application No. PCT/US2011/065936, Jun. 1, 2012, 19 pages.
Monograph—Bacillus subtilis strain QST713, vol. 1, Rappateur Member State Germany, pp. 1-161, May 15, 2001.

\* cited by examiner

BIOCONTROL OF NEMATODES

RELATED APPLICATIONS

This application claims the benefit of the following provisional patent applications under 35 U.S.C. Section 119: U.S. Provisional Application No. 61/511,508, filed on Jul. 25, 2011, U.S. Provisional Application No. 61/556,016, filed on Nov. 4, 2011, and U.S. Provisional Application No. 61/661,763, filed on Jun. 19, 2012. Each of the aforementioned provisional patent applications are incorporated by reference in their entirety.

FIELD OF INVENTION

The present invention relates to control of plant parasitic nematodes.

BACKGROUND OF INVENTION

Plant parasitic nematodes cause significant damage to a wide variety of crops, resulting in global crop yield losses estimated to range from 5% to 12% annually. Root damage by nematodes is very common and leads to stunted plants, which have smaller root systems, show symptoms of mineral deficiencies in their leaves and wilt easily. Damage by nematodes also predisposes plants to infection by a wide variety of plant pathogenic fungi and bacteria.

In order to combat and control nematodes, farmers typically use chemical nematicides. These range from gas and liquid fumigation, such as methyl bromide and chloropicrin, to application of organophosphates and carbamates, such as thionazin and oxamyl. Use of these chemical nematicides has been ongoing for several decades. Despite the effectiveness of the chemical nematicide in controlling target nematodes, there are serious limitations to these methods. One limitation is that chemical nematicides cannot act against nematodes that have already penetrated the root. Another limitation is the danger associated with the production and use of chemical nematicides. Chemical nematicides are highly toxic and can lead to human poisoning and death. As a result, countries have restricted and sometimes banned certain pesticides. Methyl bromide in particular is banned in most countries due to its ozone depleting effects.

Because of these restrictions and bans, there are a lack of viable nematode solutions. The present invention provides a safe and effective means to replace or lessen the use of chemical pesticides. It is also unique in providing a solution that both inhibits nematode penetration into the plant root and then prevents maturation of those nematodes that manage to overcome this initial barrier.

SUMMARY OF THE INVENTION

The present invention provides methods and compositions for the control of plant parasitic nematodes. The invention provides a method for controlling nematodes comprising applying to a plant, a plant part and/or a locus of the plant an effective amount of *Bacillus subtilis* QST713, mutants of *Bacillus subtilis* QST713 and/or metabolites of *Bacillus subtilis* QST713. In some embodiments, the *Bacillus subtilis* QST713 is applied as a fermentation product that includes the *Bacillus subtilis* QST713, its metabolites and, optionally, residual fermentation broth. In one embodiment, the fermentation product is composed substantially of *Bacillus subtilis* QST713 cells or cells of a mutant of *Bacillus subtilis* QST713.

The *Bacillus subtilis*-based compositions of the present invention reduce eggs of root knot nematodes, decrease root knot nematode plant penetration, and/or inhibit maturation of root knot nematodes that penetrate plants. In some embodiments, the target nematodes (i.e., nematodes that are controlled) are disease-causing root knot nematodes. In certain instances, the nematodes are from the species *Meloidogyne*. In other embodiments, the target nematodes of the compositions of the present invention are cyst nematodes. In certain instances, the target nematodes are from the species *Heterodera*. In other embodiments, the target nematodes are from the species *Globodera*. In other embodiments, the target nematodes are from the following species: *Paratylenchus, Pratylenchus, Paratrichodorus, Criconemella, Helicotylenchus, Meloidogyne*, and *Criconemoides*. In a particular instance the nematodes are *Helicotylenchus pseudorobustus* (Spiral HP) or *Helicotylenchus digonicus* (Spiral HD).

In some embodiments, the above-described compositions are mixed with at least one other pesticide, such as a fungicide, insecticide, nematicide or herbicide. In one embodiment, the pesticide is a nematicide. In certain embodiments a *Bacillus subtilis*-based composition of the present invention is tank mixed with a formulated nematicide that may be commercially available. In other embodiments, the *Bacillus subtilis*-based composition is mixed with an active ingredient (i.e., a compound(s) that is active against fungi, insects, nematodes or weeds) and then formulated with inerts, such that the multiple actives form one product. In one embodiment the other nematicidal active ingredient is carbamate or organophosphate. In another it is a biological nematicide.

The present inventions provides compositions comprising *Bacillus subtilis* QST713 or mutants thereof and a second nematode control agent. In some embodiments, the second nematode control agent is a carbamate or an organophosphate.

The present invention further provides any of the compositions of the present invention further comprising a formulation inert or other formulation ingredient, such as polysaccharides (starches, maltodextrins, methylcelluloses, proteins, such as whey protein, peptides, gums), sugars (lactose, trehalose, sucrose), lipids (lecithin, vegetable oils, mineral oils), salts (sodium chloride, calcium carbonate, sodium citrate), and silicates (clays, amorphous silica, fumed/precipitated silicas, silicate salts). In some embodiments, such as those in which the compositions are applied to soil, the compositions of the present invention comprise a carrier, such as water or a mineral or organic material, such as peat, which facilitates incorporation of the compositions into the soil. In some embodiments, such as those in which the composition is used for seed treatment or as a root dip, the carrier is a binder or sticker that facilitates adherence of the composition to the seed or root. In another embodiment in which the compositions are used as a seed treatment the formulation ingredient is a colorant. In other compositions, the formulation ingredient is a preservative.

In some embodiments the compositions are applied to plants, plant parts, or loci of the plants, such as soil, prior to planting. In other embodiments the compositions are applied at planting. In still others the compositions are applied after planting.

In certain embodiments, application of the compositions is preceded by a step comprising identifying that the plant and/or plant locus for growth needs treatment. In some embodiments, identifying includes determining that the locus for plant growth exceeds the economic threshold for nematode infestation.

In some embodiments, the present invention encompasses a kit that includes *Bacillus subtilis* QST713 or mutants thereof and instructions for its use as a nematicide. In some embodiments these instructions are a product label. In some embodiments, the instructions direct the user to use the *Bacillus subtilis* QST713 or a mutant thereof at a rate of between about $2\times10^{12}$ to about $6\times10^{13}$ cfu per acre. In some embodiments, these instructions are for use of the *Bacillus subtilis* as a nematicide in combination with a chemical nematicide. In certain instances, the instructions direct the user to use the chemical nematicide at a rate that is lower than the rate recommended on a product label for the chemical nematicide when used as a stand-alone treatment. In some other embodiments, the instructions may direct the user to apply the *Bacillus subtilis* QST713 or mutants thereof to soil in contact with plant roots, to soil at the base of the plant, or to the soil within a specific distance around the base of the plant (e.g., within a distance of about 5 cm, about 10 cm, about 15 cm, about 20 cm, about 25 cm, about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, or more around the base of the plant). The instructions may also direct the user to make multiple applications of the *Bacillus subtilis* QST713 or mutants thereof at intervals of from about 10 to about 18 days and/or at a rate of about $7\times10^5$ to about $1\times10^7$ cfu per gram of soil per application. The instructions may further direct the user to use the *Bacillus subtilis* QST713 or mutants thereof in combination with the chemical nematicide at planting and to use *Bacillus subtilis* QST713 or mutants thereof alone in subsequent applications. In one embodiment, the instructions direct the user to apply the *Bacillus subtilis* QST713 or mutants thereof as a single application at a rate of about $7\times10^5$ to about $1\times10^7$ cfu per gram of soil. In another embodiment, the instructions direct the user to apply the *Bacillus subtilis* QST713 or mutants thereof as multiple applications at a rate of about $1\times10^5$ to about $3\times10^6$ cfu per gram of soil.

DETAILED DESCRIPTION OF THE INVENTION

Figure 1:
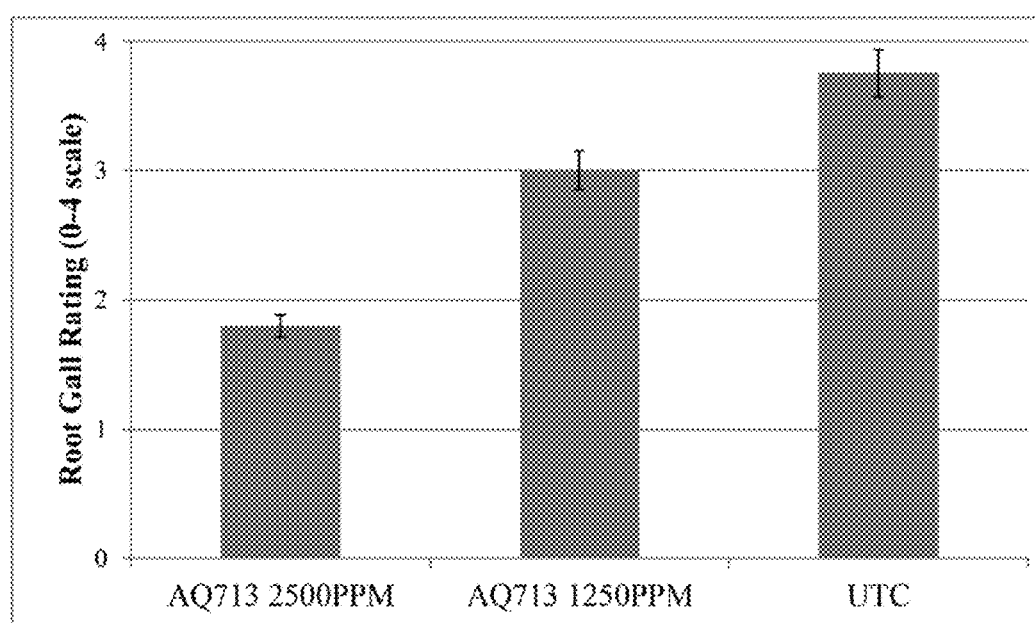
FIG. 1 shows the effect of QST713 whole broth treatment on galling of roots infested with root knot nematodes. Note that QST713 whole broth is designated as AQ713 in this and other figures. The untreated control is designated as "UTC" in the figure.

All publications, patents and patent applications, including any drawings and appendices herein, are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

The SERENADE® product (EPA Registration No. 69592-12) contains a unique, patented strain of *Bacillus subtilis* (strain QST713) and many different lipopeptides that work synergistically to destroy disease pathogens and provide superior antimicrobial activity. The SERENADE® product is used to protect plants such as vegetables, fruit, nut and vine crops against diseases such as Fire Blight, *Botrytis*, Sour Rot, Rust, *Sclerotinia*, Powdery Mildew, Bacterial Spot and White Mold. The SERENADE products are available as either liquid or dry formulations which can be applied as a foliar and/or soil treatment. Copies of EPA Master Labels for SERENADE® products, including SERENADE® ASO, SERENADE® MAX, and SERENADE SOIL °, are publicly available through National Pesticide Information Retrieval System's (NPIRS®) USEPA/OPP Pesticide Product Label System (PPLS).

The SERENADE® ASO (Aqueous Suspension-Organic) product contains 1.34% of dried QST713 as an active ingredient and 98.66% of other ingredients. The SERENADE® ASO product is formulated to contain a minimum of $1\times10^9$ cfu/g of QST713 while the maximum amount of QST713 has been determined to be $3.3\times10^{10}$ cfu/g. Alternate commercial names for the SERENADE® ASO product include SERENADE BIOFUNGICIDE®, SERENADE SOIL® and SERENADE® GARDEN DISEASE. For further information, see the U.S. EPA Master Labels for SER- ENADE® ASO dated Jan. 4, 2010 and SERENADE SOIL®, each of which is incorporated by reference herein in its entirety.

The SERENADE® MAX product contains 14.6% of dried QST713 as an active ingredient and 85.4% of other ingredients. The SERENADE® MAX product is formulated to contain a minimum of $7.3 \times 10^9$ cfu/g of QST713 while the maximum amount of QST713 has been determined to be $7.9 \times 10^{10}$ cfu/g. For further information, see the U.S. EPA Master Label for SERENADE® MAX, which is incorporated by reference herein in its entirety.

*Bacillus subtilis* QST713, its mutants, its supernatants, and its lipopeptide metabolites, and methods for their use to control plant pathogens and insects are fully described in U.S. Pat. Nos. 6,060,051; 6,103,228; 6,291,426; 6,417,163; and 6,638,910; each of which is specifically and entirely incorporated by reference herein for everything it teaches. In these U.S. Patents, the strain is referred to as AQ713, which is synonymous with QST713. *Bacillus subtilis* QST713 has been deposited with the NRRL on May 7, 1997, under the provisions of the Budapest Treaty on the International Recognition of the Deposit of Microorganisms for the Purpose of Patent Procedure under Accession Number B21661. Any references in this specification to QST713 refer to *Bacillus subtilis* QST713 (aka AQ713) as present in the SERENADE products, deposited under NRRL Accession No. B21661, or prepared in bioreactors or shake flasks under conditions that simulate production of the SERENADE® product.

The above-referenced patents describe testing of the supernatant of *Bacillus subtilis* QST713 whole broth against the N2 strain of the nematode *Caenorhabditis elegans*. Such tests showed that the supernatant lacked nematicidal activity.

At the time of filing U.S. patent application Ser. No. 09/074,870 in 1998, which corresponds to the above patents, the QST713 strain was designated as a *Bacillus subtilis* based on classical, physiological, biochemical and morphological methods. Taxonomy of the *Bacillus* species has evolved since then, especially in light of advances in genetics and sequencing technologies, such that species designation is based largely on DNA sequence rather than the methods used in 1998. After aligning protein sequences from *B. amyloliquefaciens* FZB42, *B. subtilis* 168 and QST713, approximately 95% of proteins found in *B. amyloliquefaciens* FZB42 are 85% or greater identical to proteins found in QST713; whereas only 35% of proteins in *B. subtilis* 168 are 85% or greater identical to proteins in QST713. However, even with the greater reliance on genetics, there is still taxonomic ambiguity in the relevant scientific literature and regulatory documents, reflecting the evolving understanding of *Bacillus* taxonomy over the past 15 years. For example, a pesticidal product based on *B. subtilis* strain FZB24, which is as closely related to QST713 as is FZB42, is classified in documents of the Environmental Protection Agency as *B. subtilis* var. *amyloliquefaciens*. Due to these complexities in nomenclature, this particular *Bacillus* species is variously designated, depending on the document, as *B. subtilis*, *B. amyloliquefaciens*, and *B. subtilis* var. *amyloliquefaciens*. Therefore, we have retained the *B. subtilis* designation of QST713 rather than changing it to *B. amyloliquefaciens*, as would be expected currently based solely on sequence comparison and inferred taxonomy.

The term "mutant" refers to a genetic variant derived from QST713. In one embodiment, the mutant has all the identifying characteristics of QST713. In a particular instance, the mutant controls nematodes at least as well as the parent QST713 strain. In another embodiment, mutants are genetic variants having a genomic sequence that has greater than about 85%, greater than about 90%, greater than about 95%, greater than about 98%, or greater than about 99% sequence identity to the QST713 strain. Mutants may be obtained by treating QST713 cells with chemicals or irradiation or by selecting spontaneous mutants from a population of QST713 cells (such as phage resistant mutants) or by other means well known to those practiced in the art.

Compositions of the present invention can be obtained by culturing *Bacillus subtilis* QST713 or mutants thereof according to methods well known in the art, including by using the media and other methods described in U.S. Pat. No. 6,060,051. Conventional large-scale microbial culture processes include submerged fermentation, solid state fermentation, or liquid surface culture. Towards the end of fermentation, as nutrients are depleted, *Bacillus subtilis* cells begin the transition from growth phase to sporulation phase, such that the final product of fermentation is largely spores, metabolites and residual fermentation medium. Sporulation is part of the natural life cycle of *Bacillus subtilis* and is generally initiated by the cell in response to nutrient limitation. Fermentation is configured to obtain high levels of colony forming units of *Bacillus subtilis* and to promote sporulation. The bacterial cells, spores and metabolites in culture media resulting from fermentation may be used directly or concentrated by conventional industrial methods, such as centrifugation, tangential-flow filtration, depth filtration, and evaporation. Fermentation broth and broth concentrate are both referred to herein as "fermentation products." Compositions of the present invention include fermentation products. In some embodiments, the concentrated fermentation broth is washed, for example, via a diafiltration process, to remove residual fermentation broth and metabolites.

The fermentation broth or broth concentrate can be dried with or without the addition of carriers using conventional drying processes or methods such as spray drying, freeze drying, tray drying, fluidized-bed drying, drum drying, or evaporation.

The resulting dry products may be further processed, such as by milling or granulation, to achieve a specific particle size or physical format. Carriers, described below, may also be added post-drying.

Cell-free preparations of fermentation broth of the novel variants and strains of *Bacillus* of the present invention can be obtained by any means known in the art, such as extraction, centrifugation and/or filtration of fermentation broth. Those of skill in the art will appreciate that so-called cell-free preparations may not be devoid of cells but rather are largely cell-free or essentially cell-free, depending on the technique used (e.g., speed of centrifugation) to remove the cells. The resulting cell-free preparation may be dried and/or formulated with components that aid in its application to plants or to plant growth media. Concentration methods and drying techniques described above for fermentation broth are also applicable to cell-free preparations.

Metabolites of *Bacillus subtilis* can be obtained according to the methods set forth in U.S. Pat. No. 6,060,051. The term "metabolites" as used herein may refer to semi-pure and pure or essentially pure metabolites, or to metabolites that have not been separated from *Bacillus subtilis*. In some embodiments, after a cell-free preparation is made by centrifugation of fermentation broth, the metabolites may be purified by size exclusion filtration such as the Sephadex resins including LH-20, G10, and G15 and G25 that group metabolites into different fractions based on molecular weight cut-off, such as molecular weight of less than about 2000 daltons, less than about 1500 daltons, less than about 1000 daltons and so on, as the lipopeptides are between 800 daltons and 1600 daltons.

Concentration methods and drying techniques described above for formulation of fermentation broth are also applicable to metabolites.

Compositions of the present invention may include formulation inerts added to compositions comprising cells, cell-free preparations or metabolites to improve efficacy, stability, and usability and/or to facilitate processing, packaging and end-use application. Such formulation inerts and ingredients may include carriers, stabilization agents, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the carrier is a binder or adhesive that facilitates adherence of the composition to a plant part, such as a seed or root. See, for example, Taylor, A. G., et al., "Concepts and Technologies of Selected Seed Treatments", Annu. Rev. Phytopathol. 28: 321-339 (1990). The stabilization agents may include anti-caking agents, anti-oxidation agents, desiccants, protectants or preservatives. The nutrients may include carbon, nitrogen, and phosphors sources such as sugars, polysaccharides, oil, proteins, amino acids, fatty acids and phosphates. The physical property modifiers may include bulking agents, wetting agents, thickeners, pH modifiers, rheology modifiers, dispersants, adjuvants, surfactants, antifreeze agents or colorants. In some embodiments, the composition comprising cells, cell-free preparation or metabolites produced by fermentation can be used directly with or without water as the diluent without any other formulation preparation. In some embodiments, the formulation inerts are added after concentrating fermentation broth and during and/or after drying.

Compositions of the present invention may include carriers, which are inert formulation ingredients added to compositions comprising a lipopeptide-containing fermentation product, cell-free preparations of lipopeptides or purified, semi-purified or crude extracts of lipopeptides to improve recovery, efficacy, or physical properties and/or to aid in packaging and administration. Such carriers may be added individually or in combination.

The compositions of the present invention may be mixed with and/or used in rotation with other chemical and non-chemical additives, adjuvants and/or treatments, wherein such treatments include but are not limited to chemical and non-chemical fungicides, insecticides, miticides, nematicides, fertilizers, nutrients, minerals, auxins, growth stimulants and the like.

Nematicides with which the *Bacillus subtilis*-based compositions of the present invention may be mixed may be chemical or biological nematicides. The term "chemical nematicide," as used herein, excludes fumigants, and the term "fumigants" encompasses broad spectrum pesticidal chemicals that are applied to soil pre-planting and that diffuse through the soil (in soil air and/or soil water) and may be applied as gases, such as methyl bromide, volatile liquids, such as chloropicrin, or volatile solids, such as dazomet.

In some embodiments, the chemical or biological nematicide is a commercially available formulated product and is tank mixed and/or used in rotation with the compositions of the present invention. In other embodiments, the active ingredient (without inerts) of the chemical or biological nematicide is mixed with the *Bacillus subtilis* QST713-based composition prior to formulation (with inerts) such that the compositions form one formulated product.

Chemical nematicides used in such mixtures or rotational programs are carbamates, oxime carbamates and organophosphorous nematicides. Carbamate nematicides include benomyl, carbofuran (FURADAN®), carbosulfan and cloethocarb. Oxime carbamates include alanycarb, aldicarb (TEMIK® or as part of the AVICTA® Complete Pak seed treatment from Syngenta), aldoxycarb, (STANDAK®), oxamyl (VYDATE®), thiodicarb (part of the AERIS® seed-applied system from Bayer CropScience), and tirpate. Organophosphorous nematicides include fensulfothion (DANSANIT®), ethoprop, (MOCAP®), diamidafos, fenamiphos, fosthietan, phosphamidon, cadusafos, chlorpyrifos, dichlofenthion, dimethoate, fosthiazate, heterophos, isamidofos, isazofos, phorate, phosphocarb, terbufos, thionazin, triazophos, imicyafos, and mecarphon. Parenthetical names following each compound are representative commercial formulations of each of the above chemicals. Other chemical nematicides useful for such mixtures include spirotetramat (MOVENTO®), MON37400 nematicide and fipronil.

Biological nematicides used in such mixtures or rotational programs include chitin and urea mixtures, compost extracts and teas (both aerated and nonaerated); compositions comprising the fungus *Myrothecium verrucaria* and/or metabolites therefrom (commercially available as DITERA®), compositions comprising the fungus *Paecilomyces lilacinus* (commercially available as, for example, MELOCON® or BIOACT®); compositions comprising the bacterium *Pasteuria* including *P. usgae* (commercially available as, for example, ECONEM®); compositions comprising bacteria from the *Bacillus* sp., including *Bacillus firmus* (including the strain deposited as CNMC 1-1582 with the Collection Nationale de Cultures de Microorganismes, Institute Pasteur, France on May 29, 1995, and commercially available as, for example, VOTIVO®), *Bacillus subtilis*, *Bacillus amyloliquefaciens*, *Bacillus pumilus* (including the strain deposited with NRRL as B-30087 on Jan. 14, 1999 and its mutants) and *Bacillus cereus*; and compositions comprising nematicidal *Streptomycete* sp., such as *Streptomyces lydicus* (commercially available as ACTINOVATE®). Biological nematicides also include botanically-based nematicides such as products based on neem plants (including seeds or oil from the plants) or azidirachtin, a secondary metabolite of neem seeds, sesame oil-based products (such as DRAGON-FIRE®), carvacrol, and products based on plant extracts (such as NEMA-Q®, obtained from the *Quillaja saponaria* tree of Chile). Biological nematicides also include isolated compounds produced by bacteria, such as the mectins, which are produced by *Streptomyces avermentilis*, including abamectin (consisting of a combination of abamectin B1a and B1b) and avermectin B2a, and the harpin proteins, originally identified in *Erwinia amylovora*, including harpinEA and harpin$_{\alpha\beta}$.

Compositions of the present invention are useful to control plant parasitic nematodes, such as, for example, root-knot, cyst, lesion and ring nematodes, including *Meloidogyne* spp., *Heterodera* spp., *Globodera* spp., *Pratylenchus* spp. and *Criconemella* sp. Compositions are also useful to control *Tylenchulus semipenetrans*, *Trichodorus* spp., *Longidorus* spp., *Rotylenchulus* spp., *Xiphinema* spp., *Belonolaimus* spp. (such as *B. longicaudatus*), *Criconemoides* spp., *Tylenchorhynchus* spp., *Hoplolaimus* spp., *Rotylenchus* spp., *Helicotylenchus* spp. (such as *Helicotylenchus* pseudorobustus (Spiral HP) and *Helicotylenchus digonicus* (Spiral HD)), *Radopholus* spp. (such as *R. citrophilis* and *R. similis*), *Ditylenchus* spp., *Paratrichodorus* spp. and other plant parasitic nematodes. In some embodiments the targets are cyst nematodes, such as *Heterodera glycines* (soybean cyst nematodes), *Heterodera schachtii* (beet cyst nematode), *Heterodera avenae* (Cereal cyst nematode), *Meloidigyne incognita* (Cotton (or southern) root knot nematode), *Globodera rostochiensis* and *Globodera pallida* (potato cyst nematodes). In other embodiments, the targets are root knot nematodes, such as *M. incognita* (cotton root knot nematode), *M. javanica* (Javanese root knot nematode), *M. hapla* (Northern root knot nematode), and *M. arenaria* (peanut root knot nematode).

The term "control," as used herein, means killing, reducing in numbers, and/or reducing growth, feeding or normal physiological development, including, for root knot nematodes, the ability to penetrate roots and to develop within roots. An effective amount is an amount able to noticeably reduce nematode growth, feeding, root penetration, maturation in the root, and/or general normal nematode physiological development and/or plant host symptoms resulting from nematode infection, such as galling or reduced root and/or plant growth. In some embodiments symptoms and/or nematodes are reduced by at least about 5%, at least about 10%, at least about 20%, at least about 30%, at least about 40%, at least about 50%, at least about 60%, at least about 70%, at least about 80%, or at least about 90%.

Compositions of the present invention are used to treat a wide variety of agricultural and/or horticultural crops, including those grown for seed, produce, and landscaping. Representative plants that can be treated using the compositions of the present invention include but are not limited to the following: bulb vegetables; cereal grains; citrus fruits (such as grapefruit, lemon, and orange); cotton and other fiber crops; cucurbits; fruiting vegetables; leafy vegetables (such as celery, head and leaf lettuce, and spinach); legumes; oil seed crops; peanut; pome fruit (such as apple and pear); stone fruits (such as almond, pecan, and walnut); root vegetables; tuber vegetables; corm vegetables; tobacco, strawberry and other berries; cole crops (such as broccoli and cabbage); grape; pineapple; and flowering plants, bedding plants, and ornamentals (such as fern and hosta). Compositions of the present invention are also used to treat perennial plants, including plantation crops such as banana and coffee and those present in forests, parks or landscaping.

Compositions described herein are applied to a plant, a plant part, such as a seed, root, rhizome, corm, bulb, or tuber, and/or a locus on which the plant or the plant parts grow, such as soil, in order to control plant parasitic nematodes. The compositions of the present invention may be administered as a foliar spray, as a seed/root/tuber/rhizome/bulb/corm treatment and/or as a soil treatment. The seeds/root/tubers/rhizomes/bulbs/corms can be treated before planting, during planting or after planting.

Compositions described herein are also applied to a plant, a plant part, such as a seed, root rhizome, corm, bulb, or tuber, and/or a locus on which the plant or the plant parts grow, such as soil, in order to control nematodes, thereby increasing crop yield. In some embodiments, crop yield is increased by at least about 5%, in others by at least about 10%, in still others at least about 15%, and in still others by at least about 20%.

When used as a seed treatment, the compositions of the present invention are applied at a rate of about $1 \times 10^2$ to about $1 \times 10^9$ cfu/seed, depending on the size of the seed. In some embodiments, the application rate is about $1 \times 10^3$ to about $1 \times 10^8$ cfu/seed or about $1 \times 10^4$ to about $1 \times 10^7$ cfu/seed.

The present compositions may also be applied as a root dip at a rate of about $1 \times 10^3$ to about $1 \times 10^8$ cfu/plant root system.

When used as a soil treatment, the compositions of the present invention can be applied as a soil surface drench, shanked-in, injected and/or applied in-furrow or by mixture with irrigation water. The rate of application for drench soil treatments, which may be applied at planting, during or after seeding, or after transplanting and at any stage of plant growth, is about $4 \times 10^7$ to about $8 \times 10^{14}$ cfu per acre or about $4 \times 10^9$ to about $8 \times 10^{13}$ cfu per acre or about $4 \times 10^{11}$ to about $8 \times 10^{12}$ cfu per acre or about $2 \times 10^{12}$ to about $6 \times 10^{13}$ cfu per acre or about $2 \times 10^{12}$ to about $3 \times 10^{13}$ cfu per acre. In some embodiments, the rate of application is about $1 \times 10^{12}$ to about $6 \times 10^{12}$ cfu per acre or about $1 \times 10^{13}$ to about $6 \times 10^{13}$ cfu per acre. The rate of application for in-furrow treatments, applied at planting, is about $2.5 \times 10^{10}$ to about $5 \times 10^{11}$ cfu per 1000 row feet. In some embodiments, the rate of application is about $6 \times 10^{10}$ to about $3 \times 10^{12}$ cfu per 1000 row feet or about $6 \times 10^{10}$ to about $4 \times 10^{11}$ cfu per 1000 row feet or about $6 \times 10^{11}$ to about $3 \times 10^{12}$ cfu per 1000 row feet or about $6 \times 10^{11}$ to about $4 \times 10^{12}$ cfu per 1000 row feet. Those of skill in the art will understand how to adjust rates for broadcast treatments and other less common soil treatments.

The compositions of the present invention can be introduced to the soil before planting or before germination of the seed. The compositions of the present invention can also be introduced to the soil in contact with plant roots, to soil at the base of the plant, or to the soil around the base of the plant (e.g., within a distance of about 5 cm, about 10 cm, about 15 cm, about 20 cm, about 25 cm, about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, or more around or below the base of the plant). The compositions may be applied by utilizing a variety of techniques including, but not limited to, drip irrigation, sprinklers, soil injection or soil drenching. The compositions may also be applied to soil and/or plants in plug trays or to seedlings prior to transplanting to a different plant locus. When applied to the soil in contact with the plant roots, to the base of the plant, or to the soil within a specific distance around the base of the plant, including as a soil drench treatment, the composition may be applied as a single application or as multiple applications. The compositions may be applied at the rates set forth above for drench treatments or a rate of about $1 \times 10^5$ to about $1 \times 10^8$ cfu per gram of soil, $1 \times 10^5$ to about $1 \times 10^7$ cfu per gram of soil, $1 \times 10^5$ to about $1 \times 10^6$ cfu per gram of soil, $7 \times 10^5$ to about $1 \times 10^7$ cfu per gram of soil, $1 \times 10^6$ to about $5 \times 10^6$ cfu per gram of soil, or $1 \times 10^5$ to about $3 \times 10^6$ cfu per gram of soil. In one embodiment, the compositions of the present invention are applied as a single application at a rate of about $7 \times 10^5$ to about $1 \times 10^7$ cfu per gram of soil. In another embodiment, the compositions of the present invention are applied as a single application at a rate of about $1 \times 10^6$ to about $5 \times 10^6$ cfu per gram of soil. In other embodiments, the compositions of the present invention are applied as multiple applications at a rate of about $1 \times 10^5$ to about $3 \times 10^6$ cfu per gram of soil.

When the compositions of the present invention are applied as multiple applications, these applications may take place at intervals of from about 1 to about 28 days, of from about 1 to about 21 days, of from about 1 to about 14 days, of from about 7 to about 28 days, of from about 7 to about 21 days, of from about 7 to about 14 days, or of from about 10 to about 18 days.

*Bacillus subtilis*-based compositions of the present invention may be applied independently or in combination with one or more other nematicides, such as chemical and biological nematicides. In some embodiments, *Bacillus subtilis* QST713 is co-formulated with at least one other nematicide and the co-formulated product is applied to the plant or plant locus. In some other embodiments, the *Bacillus subtilis*-based compositions are tank mixed with commercially available formulations of the chemical or biological nematicides and applied to plants and plant loci. In other embodiments, the *Bacillus subtilis*-based compositions of the present invention are applied to plants and/or plant loci immediately before or after the commercially available formulations of the chemical or biological nematicides. In other embodiments, the *Bacillus subtilis*-based compositions of the present invention are applied to plants and/or plant loci in rotation with the commercially available formulations of the chemical or biological nematicides. In a rotational program involving several applications of nematicides, the compositions of the present invention may be applied alone or in combination with other nematicides. In one instance, the *Bacillus subtilis*-based compositions are applied as a seed treatment or as an in-furrow or drench treatment, as discussed in more detail below.

While applicants do not wish to be held to any particular theory, it is thought that *Bacillus subtilis* QST713 controls nematodes by Induced Systemic Resistance (ISR) in the treated plants. For an explanation of ISR, see Bakker, P. A. H. M., "Induced Systemic Resistance by Fluorescent *Pseudomonas* spp." *Phytophathology* 97(2): 239-243 (2007). ISR may take effect only after a certain lag period between the time of treatment with *Bacillus subtilis* QST713 and subsequent nematode challenge to the plant. In some embodiments the *Bacillus subtilis*-based compositions are applied in combination with a second nematicide at planting and the *Bacillus subtilis*-based compositions are applied alone or in combinations with another nematicide in subsequent applications. The initial treatment with the second nematicide may protect the plant during the lag period until the *Bacillus subtilis*-based compositions have triggered ISR. In some instances of the above embodiments, the commercially available formulation of the second chemical or biological nematicide is applied at a rate below the label recommendation for use as a stand-alone nematicide treatment. In one embodiment, *Bacillus subtilis* QST713 is applied with oxamyl (VYDATE®) at planting and the *Bacillus subtilis* QST713 is applied alone in subsequent applications.

In other embodiments, the *Bacillus*-based compositions of the present invention are applied to plants and/or plant loci following application of a fumigant. Fumigants can be applied by shank injection, generally a minimum of 8 inches below the soil surface. Liquid formulations of fumigants can also be applied through surface drip chemigation to move the fumigant to a depth of 8 inches or more below the soil surface. Treated soil beds are covered with a plastic tarp to retain the fumigant in the soil for several days. This is done before planting and allowed to air out prior to planting. The *Bacillus*-based compositions described herein would be applied after such air-out period either prior to, at the time of, or post-planting. In some instances, the fumigants are applied at a rate that is less than the rate recommended on the product label.

Chemical and biological nematicides are described above. Fumigant nematicides include halogenated hydrocarbons, such as chloropicrin (CHLOR-O-PIC®); methyl bromide (METH-O-GAS®) and combinations thereof (such as BROM-O-GAS® and TERR-O-GAS®); 1,3-dichloropropene (TELONE® II, TELONE® EC, CURFEW®) and combinations of 1,3-dichloropropene with chloropicrin (TELONE® C-17, TELONE® C-35, and INLINE®); methyl iodide (MIDAS®); methyl isocyanate liberators, such as sodium methyl dithiocarbamate (VAPAM®, SOIL-PREP®, METAM-SODIUM®); combinations of 1,3 dichloropropoene and methyl isothiocyanate (VORLEX®); and carbon disulfide liberators, such as sodium tetrathiocarbonate (ENZONE®); and dimethyl disulphide or DMDS (PALADINO®). Example commercial formulations of each of the above fumigants are provided in parentheses after the chemical name(s).

Compositions of the present invention may also be applied as part of an integrated pest management ("IPM") program. Such programs are described in various publications, especially by university cooperative extensions. Such programs include crop rotation with crops that cannot host the target nematode, cultural and tillage practices, and use of transplants. For example, the *Bacillus*-based compositions could be applied after a season of growth with mustard or other nematode suppressive crop.

In some embodiments, application of the compositions of the present invention to plants, plant parts or plant loci is preceded by identification of a locus in need of treatment. Such identification may occur through visual identification of plants that appear chlorotic, stunted, necrotic, or wilted (i.e., that appear to have nutrient deficiencies) typically coupled with knowledge of a history of nematode problems; plant sampling; and/or soil sampling. Plant sampling may occur during the growing season or immediately after final harvest. Plants are removed from soil and their roots examined to determine the nature and extent of the nematode problem within a field. For root knot nematode, root gall severity is determined by measuring the proportion of the root system which is galled. Galls caused by root knot nematodes may be distinguished from nodules of nitrogen-fixing soil bacteria because galls are not easily separated from the root. Root knot nematode soil population levels increase with root gall severity. In some instances, the detection of any level of root galling suggests a root knot nematode problem for planting any susceptible crop, especially in or near the area of sampling. Cyst nematodes may also be identified by plant sampling and scrutiny of roots for cysts.

Soil sampling offers a means to determine the number of nematodes and/or nematode eggs infesting a certain volume of soil or roots. Soil sampling may be conducted when a problem is first suspected, at final harvest, or any time prior to planting a new crop, including prior to crop destruction of the previous crop. University cooperative extension programs offer soil sampling services, including the University of Florida, Oregon State University and the University of Nebraska-Lincoln. In addition, such programs provide guidance for how to collect samples. For example, in one method of post-harvest predictive sampling, samples are collected at a soil depth of 6 to 10 inches from 10 to 20 field locations over 5 or 10 acres (depending on value of the crop, with fewer acres sampled for higher value crops) in a regular zigzag pattern. In a method of testing established plants, root and soil samples are removed at a soil depth of 6 to 10 inches from suspect plants that are symptomatic but that are not dead or dying, i.e., decomposing.

In some embodiments, identification involves determining whether an economic threshold of nematode infestation has been reached; i.e., a point at which expected economic losses without treatment exceed treatment costs. The economic threshold varies depending on the crop, geography, climate, time of planting, soil type, and/or soil temperature. Numerous papers have been published on this topic and guidelines are available from university cooperative extension programs in different areas. See, for example, Robb, J. G., et al., "Factors Affecting the Economic Threshold for *Heterodera schachtii* Control in Sugar Beet," Economics of Nematode Control January-June 1992; Hafez, Saad L., "Management of Sugar Beet Nematode," University of Idaho Current Information Series (CIS) 1071 (1998); and *UC IPM Pest Management Guidelines: Tomato* UC ANR Publication 3470 Nematodes A. Ploeg, Nematology, UC Riverside (January 2008). Determining the economic threshold for a particular crop at a particular time of year is well within the skill set of one of ordinary skill in the art.

In some embodiments, the soil sampling reveals that the nematode infestation will cause yield that is about 80%, about 90%, or about 95% of normal for uninfested soil.

In some embodiments, the economic threshold of root knot juveniles per kilogram of soil sample is at least about 250, at least about 300, at least about 500, at least about 750, at least about 1000, at least about 2000, at least about 3000, at least about 4000, at least about 5000, or at least about 6000.

In some embodiments, the economic threshold of cyst nematode eggs and larvae per 1 cm$^3$ soil is at least about 0.5, at least about 1, at least about 2, at least about 3, at least about 4. According to Hafez (1998), supra, a cyst may be estimated as 500 viable eggs and larvae.

The following examples are given for purely illustrative and non-limiting purposes of the present invention.

EXAMPLES

Example 1

Activity of *Bacillus subtilis* QST713 Against *Meloidogyne javanica*

Studies were conducted with cucumber seeds var. Sultan to determine activity of QST713 against *Meloidogyne javanica*, root knot nematode. 50 ml centrifuge tubes containing 20 g sand and one ungerminated seed were treated with different rates of whole broth of QST713 or of the commercially available SERENADE® ASO product. The whole broth and SERENADE® ASO product differ in that the product is much more concentrated in terms of colony forming units (cfu) and metabolites, with the product having at least 1 log greater cfu than the whole broth. In addition, the product is formulated with, among other things, preservatives, such that the product is more acidic than the whole broth. To obtain whole broth cultures of QST713, seed flasks containing Luria Broth (LB) were inoculated with QST713 and grown overnight at 30° C. The next day, aliquots from each seed flask were inoculated into 200 ml of a soy-based medium in a 1 L shake flask and grown until sporulation. Briefly, the shake flask culture was maintained at a temperature between 30° C. and 32° C. and at a shaker setting of 200 to 220 rpm. After approximately 3 days of incubation, when cell growth and metabolite production had stopped, the culture broth was harvested. The treated seeds were allowed to germinate and grow in the greenhouse. Four to five days after treatment (DAT) each tube was inoculated with 100 second-stage juvenile root knot nematodes. 10 DAT the seedlings were scored for percentage root galling on a 0-4 scale, which is described in Table 1.

The roots were then stained with acid fuschin to observe nematode penetration and development and observed under a LEICA® dissecting microscope. For nematode penetration, the total nematode juveniles inside each root were counted. For nematode development, total fat juveniles including late second stage juvenile (J2's) and third stage juvenile (J3's) were counted. Penetration of nematodes into the root and nematode development after penetration were scored as detailed in Table 1. For details on techniques used, see C. O. Omwega, et al., "A Nondestructive Technique for Screening Bean Germ Plasm for Resistance to *Meloidogyne incognita*," Plant Disease (1988) 72(11): 970-972.

TABLE 1

Rating Scheme for Nematode Antagonistic Activity of Bacterial Whole Broths. The galling index was based on the percentage of root galling. The penetration scale was calculated as the mean total number of juvenile nematodes relative to the number of juvenile nematodes in the untreated control (UTC). The development scale reflects the total number of fat juvenile nematodes (late J2 stage/J3 stage) inside the root.

| Galling Index | | Penetration Scale | | Development Scale | |
| --- | --- | --- | --- | --- | --- |
| 0 | None | 0 | None | 0 | None |
| 1 | 1-24% | 1 | 1-10% | 1 | 1-3 |
| 2 | 25-49% | 2 | 11-50% | 2 | 3-10 |
| 3 | 50-74% | 3 | 51-75% | 3 | 11-30 |
| 4 | >75% | 4 | 76-100% | 4 | >30 |

Figure 2:
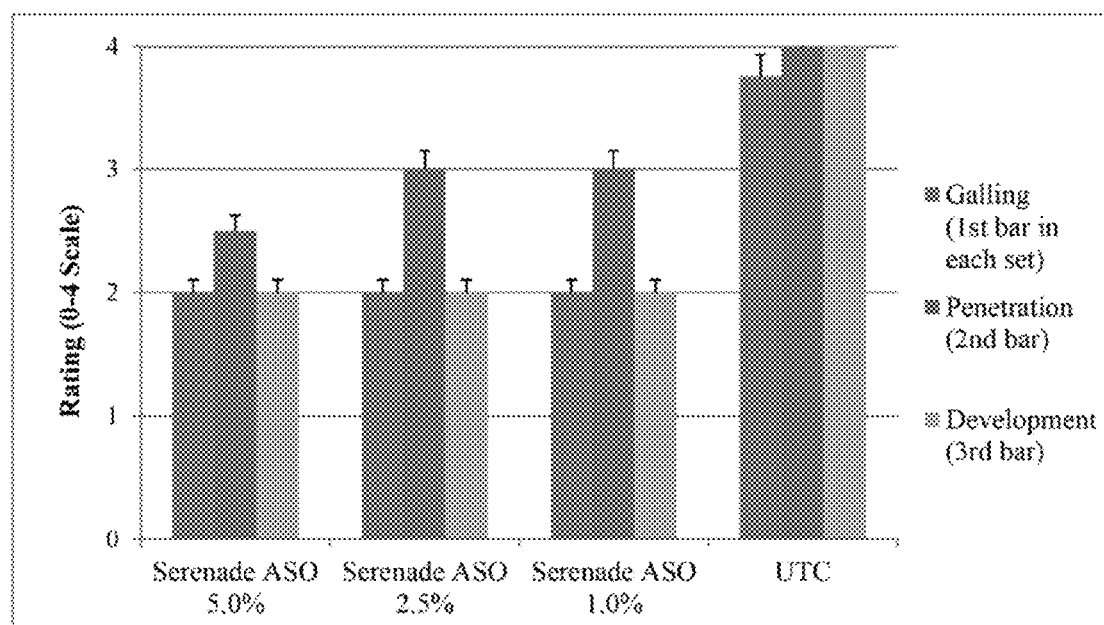
FIG. 2 shows the effect of treatment with the SERENADE® ASO product at various rates on seedlings infested with root knot nematodes. Specifically, results show extent of root galling and penetration and effects on nematode development. The first bar in each set of three bars corresponding to each treatment (SERENADE®ASO 5.0%, 2.5% and 1.0% and UTC) represents galling, the second bar represents nematode penetration and the third represents nematode development.

FIG. 1 shows that application of QST713 whole broth decreases root galling. FIG. 2 shows that application of various rates of the SERENADE® ASO product decrease galling, penetration and development compared to the untreated control. Note that because the data is based on the above rating system it is not always possible to observe a dose response.

Example 2

Efficacy of AQ713 for Control of Root-Knot Nematodes Eggs in Tomatoes

Figure 3:
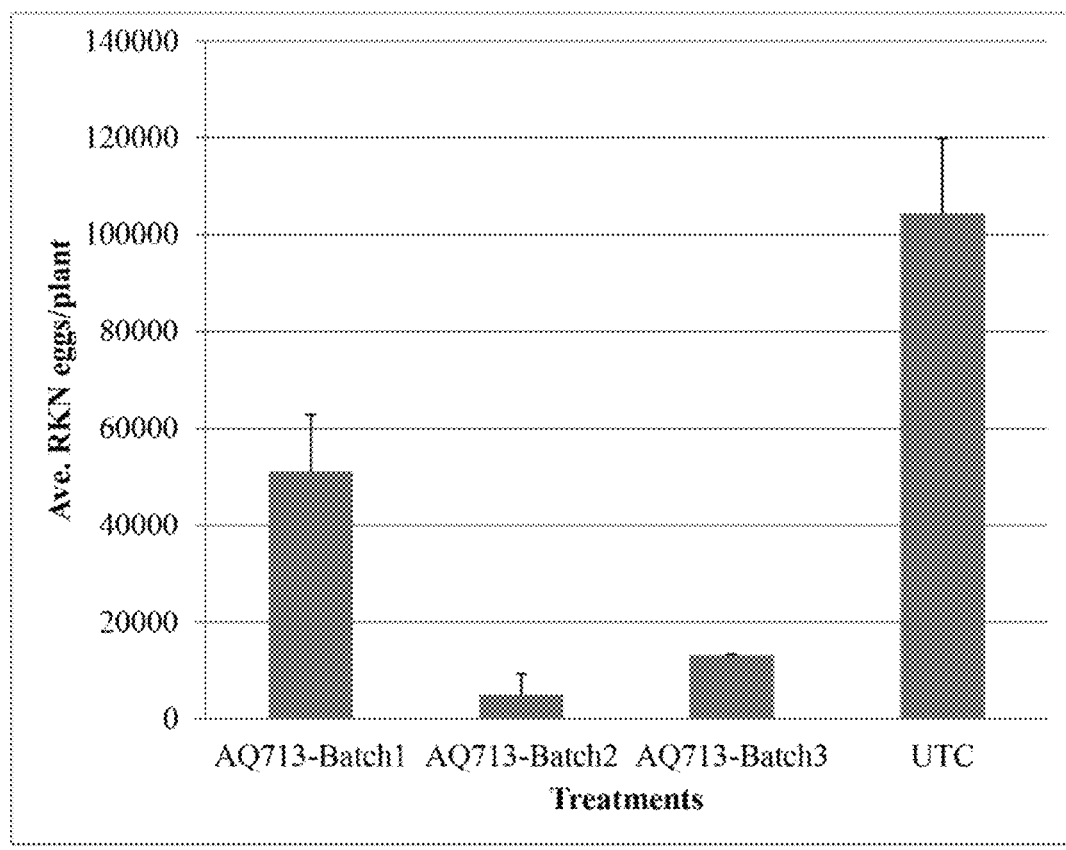
FIG. 3 represents root knot nematode eggs per plant treated with various batches of AQ713 whole broth as compared to untreated plants (designated as UTC in the figure).

Another experiment was conducted with tomato seeds to test efficacy of QST713 against root knot nematode eggs. AQ713-Batch 1 was a whole broth culture prepared as described in Example 1. AQ713-Batch2 and AQ713-Batch3 were prepared in a bioreactor. Briefly, a vial of stock culture was thawed and transferred to a sterilized flask of DIFCO® Nutrient Broth. The flask culture was then incubated on a rotary shaker at a temperature between 28° C. and 32° C. at a rotation speed of 200 to 220 rpm to promote cell growth and obtain high cell density and then added to 12 L of a soy-based growth medium in a 20 L bioreactor. The bioreactor was set at a temperature setting between 30° C. and 32° C., at an agitation setting of 500 to 1000 rpm, to a pH buffered between 6 and 8, and to an aeration between 0.5 and 1.0 VVM. After approximately 3 days of incubation, when cell growth and metabolite production had stopped, the culture broth was harvested. Three-week old tomato plants were treated with QST713 by drench. Pots were then kept in a greenhouse for ten days before being inoculated with 5000 root-knot nematode ("RKN") eggs per pot. Plants were harvested forty-two days after nematode inoculation. Eggs were collected from the roots of the tomato plants using a 1% NaOCl solution as detailed in Hussey R S, Barker K R, "A Comparison of Methods of Collecting Inocula of *Meloidogyne* spp., Including a New Technique," Plant Disease Reporter, 1973; 57:1025-1028. AQ713 decreased the number of root knot nematode eggs observed per plant. Data represents direct counts of eggs rather than a scoring system. Results as compared to an untreated sample (UTC) are shown in FIG. 3.

Example 3

Efficacy of the SERENADE SOIL® Product Against Various Nematodes

"Buried bag" studies were conducted to determine the effectiveness of the SERENADE SOIL® product against various types of nematodes in a strawberry field. Buried bag studies are commonly used to evaluate the effectiveness of soil treatments, especially fumigants. A soil sample containing a known concentration of nematodes was placed in nylon mesh bags and buried at a depth of around six to eight inches in the strawberry plant bed. Various treatments were applied as shown in Table 2. The INLINE® product was used as a positive control and in combination with the SERENADE SOIL® product.

TABLE 2

| Trt. No. | Treatment Name | Rate | Appl Code | Appl Dates |
|---|---|---|---|---|
| 1 | Untreated Check | — | | — |
| 2 | SERENADE SOIL ® | 4 qt/ac | BCD | Nov. 24, 2011, Jan. 27, 2011, Apr. 1, 2011 |
| 3 | INLINE ® followed | 20 gal/ac | A | Nov. 3, 2010 |
|   | by SERENADE SOIL ® | 4 qt/ac | BCD | Nov. 24, 2010, Jan. 27, 2011, Apr. 1, 2011 |
| 4 | INLINE ® | 20 gal/ac | A | Nov. 3, 2010 |

Bags were collected on Dec. 8, 2010, after treatment B, and the nematodes (adults and larvae) were counted. Results are shown below.

| Nematode Evaluated | Untreated Control | SERENADE SOIL ® @ 4 qts | INLINE ® @ 20 gal. | INLINE @ 20 gal + SERENADE SOIL ® @ 4 qts |
|---|---|---|---|---|
| Root-Knot (*Meloidogyne*) | 578 a | 69 b | 18 b | 20 b |
| Ring (*Criconemella*) | 1,322 a | 36 b | 10 b | 10 b |
| Pin (*Paratylenchus*) | 15 a | 2 a | 11 a | 6 a |

Means followed by same letter to do not significantly differ at P=0.05 (Student-Newman-Kewls).

Figure 4:
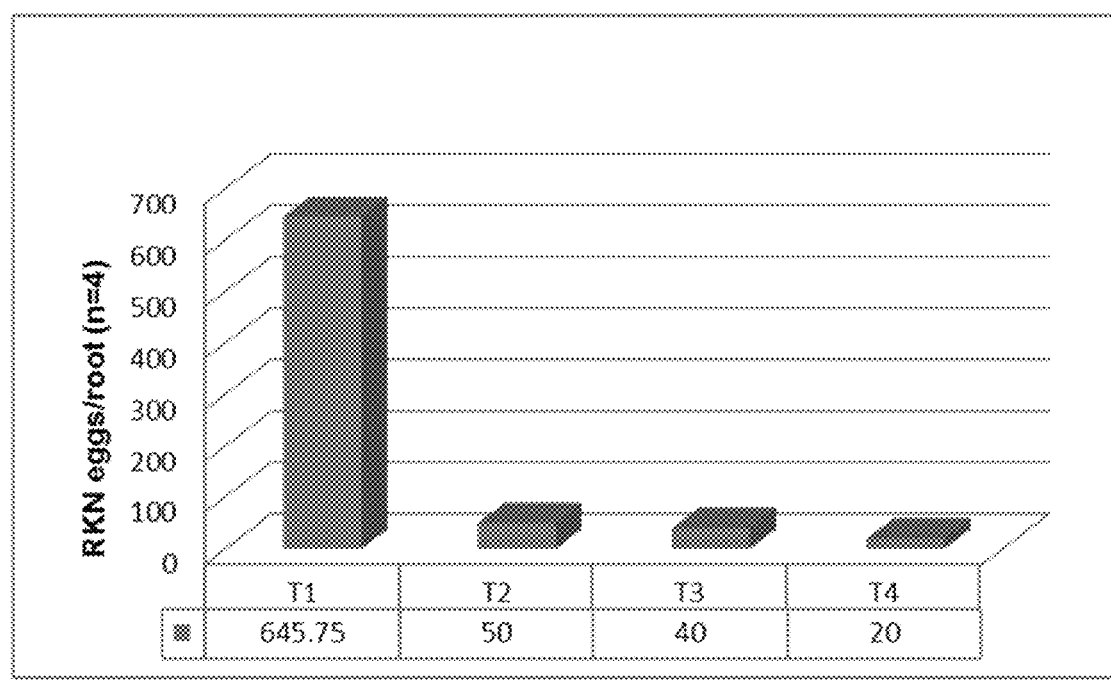
FIG. 4 represents root knot nematode eggs per plant treated with the SERENADE SOIL® product, either independently or in combination with the INLINE® product (with active ingredients of 1,3-dichloropropene+chloropicrin) as compared to untreated plants (designated as UTC) and plants treated with the INLINE® product alone. Various treatments set forth in Table 2 are designated as T1, T2, T3 and T4 in the figure.

A few weeks after the last application shown above, some plants were removed from the plots and roots analyzed for root knot nematodes, as described in Example 2. FIG. 4 shows that all treatments reduced root knot nematode eggs/root.

In subsequent experiments the SERENADE SOIL® product was shown to be effective at controlling *Paratrichodorus* sp. and *Paratylenchus* sp. in potato plants when compared to untreated control. The SERENADE SOIL® product also showed activity against *Helicotylenchus pseudorobustus* (Spiral HP), *Helicotylenchus digonicus* (Spiral HD) and *Criconemella* sp. in strawberry plants and against *Criconemoides* sp. in tomato plants and against *Paratylenchus* sp. in potatoes as compared to untreated control.

Example 4

Lag Period Between Treatment with *Bacillus subtilis* QST713 and Efficacy Against *Meloidogyne javanica*

Figure 5A:
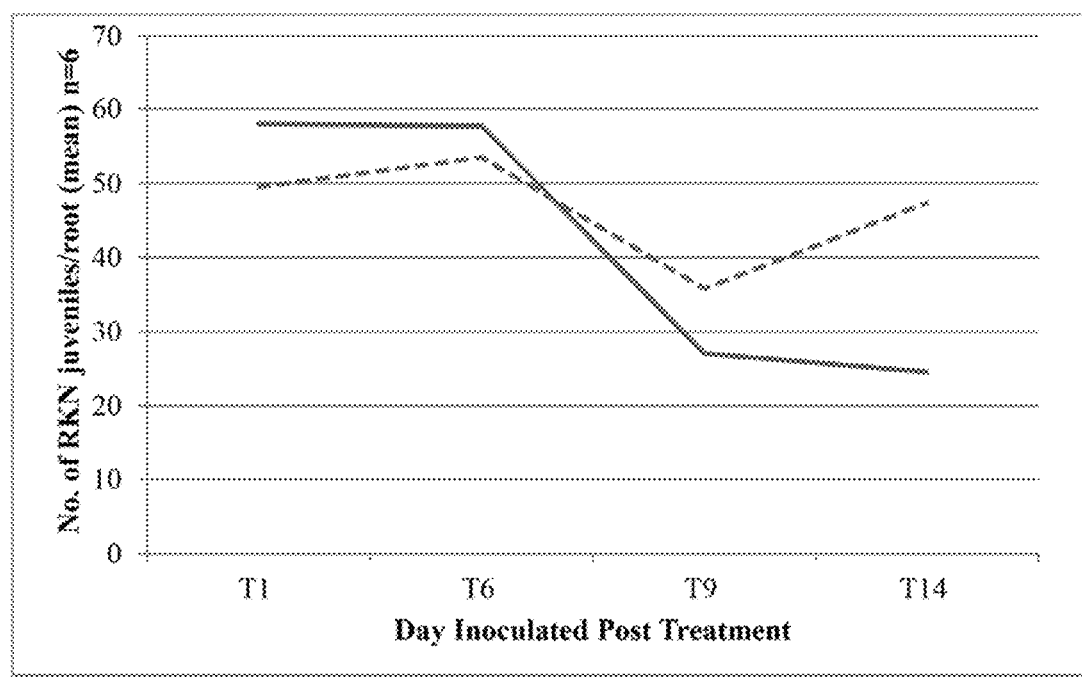
In FIG. 5A, the dotted line represents the untreated control ("UTC") while the solid line represents treatment with AQ713.
Figure 5B:
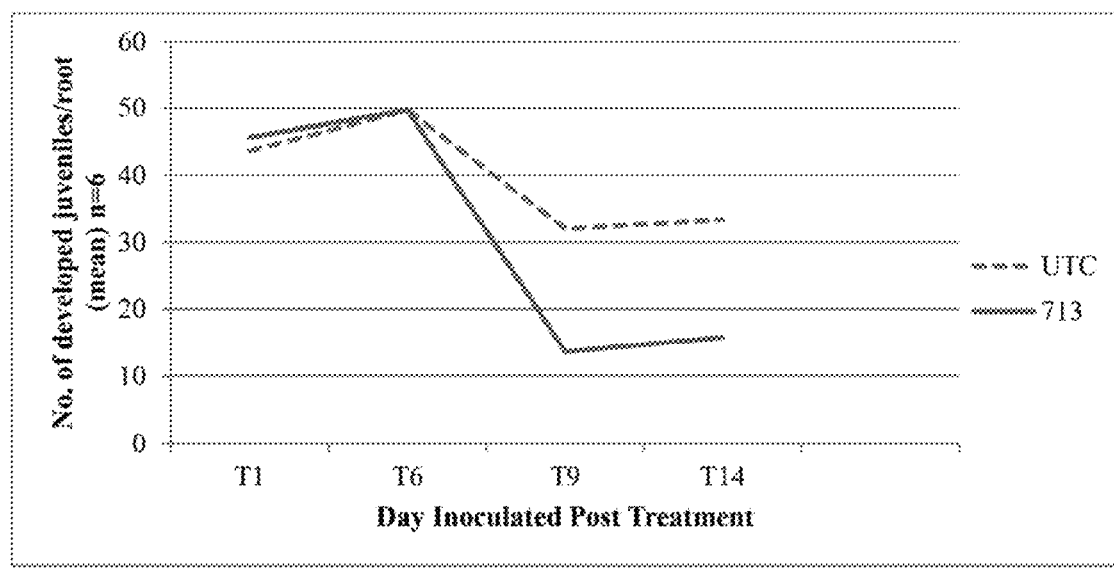
FIG. 5 represents penetration of root knot nematodes per plant root (FIG. 5A) and development of root knot nematodes per plant root (FIG. 5B) treated with AQ713 whole broth and challenged with nematode juveniles at 1-day, 6-day, 9-day, and 14-day intervals (T1, T6, T9 and T14).

The experimental techniques previously described in Example 1 were used for the following experiment with cucumber plants. Briefly, whole broth cultures of AQ713 were prepared and were used to treat cucumber seeds ($10^5$ CFU/g seed) on Day 0 (T0). The cucumber plants were challenged with nematode juveniles at 1-day, 6-day, 9-day, and 14-day intervals (T1, T6, T9 and T14). Each time point was harvested at 14 days post-inoculation (DPI) with juvenile nematodes. The number of *Meloidogyne javanica* root knot nematodes (RKN) that penetrated the roots was quantified (see FIG. 5A) as well as the number of developed juveniles (see FIG. 5B). Each data point represents the mean number of nematodes in 6 cucumber plants. AQ713 was effective at controlling RKN penetration and development as compared to untreated control (UTC) levels when there was a lag time greater than 6 days between the AQ713 treatment and nematode challenge in the cucumber plants.

Figure 6:
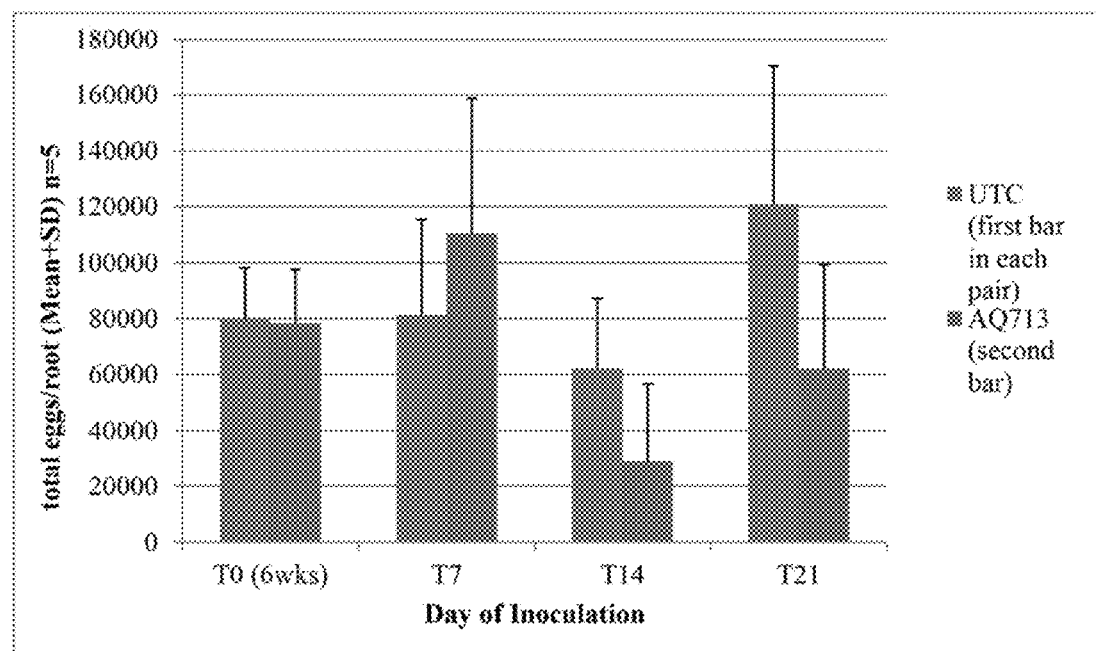
FIG. 6 represents total eggs produced by root knot nematodes per plant root after plants were drenched with AQ713 whole broth on Day 0 (T0) and were challenged with nematodes at 1, 2, or 3 weeks (T7, T14, or T21). The untreated control (UTC) is the first bar in each pair of bars provided for each inoculation date. The second bar in each pair represents results with AQ713 treatment.

To confirm the observation that AQ713 works well when there is some lag period between treatment and nematode challenge, 4-week-old tomato seedling were drenched with AQ713 whole broth ($10^5$ CFU/g sand) on Day 0 (T0) and were challenged at 1, 2, or 3 weeks (T7, T14, or T21) with 1000 RKN juveniles/pot as described in Example 2. Each time point was harvested on 42 DPI and total eggs per root were counted. Each data point represents the mean number of eggs in 5 tomato plants. The lag period between AQ713 treatment and the subsequent nematode challenge required for efficacy in decreasing RKN egg numbers in the tomato roots below untreated control (UTC) levels was about 14 days or more in this experiment (see FIG. 6).

Example 5

Figure 7A:
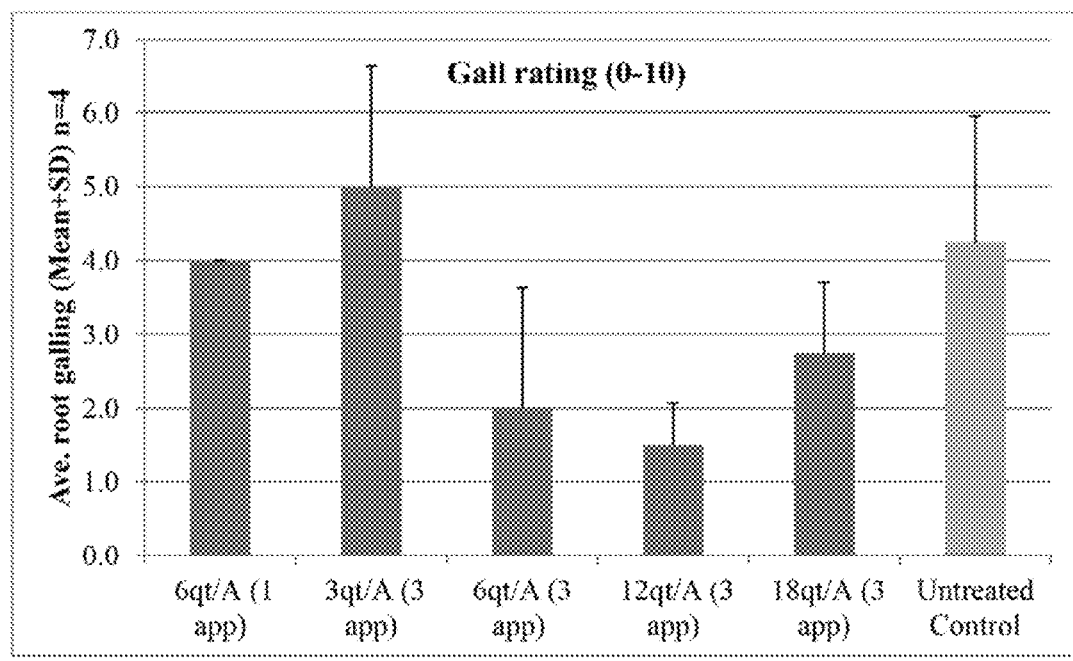
FIG. 7 represents gall rating (FIG. 7A) total eggs per root (FIG. 7B), and fresh shoot weights (FIG. 7C) of plants treated with single or multiple applications of the SERENADE® ASO product.
Figure 7B:
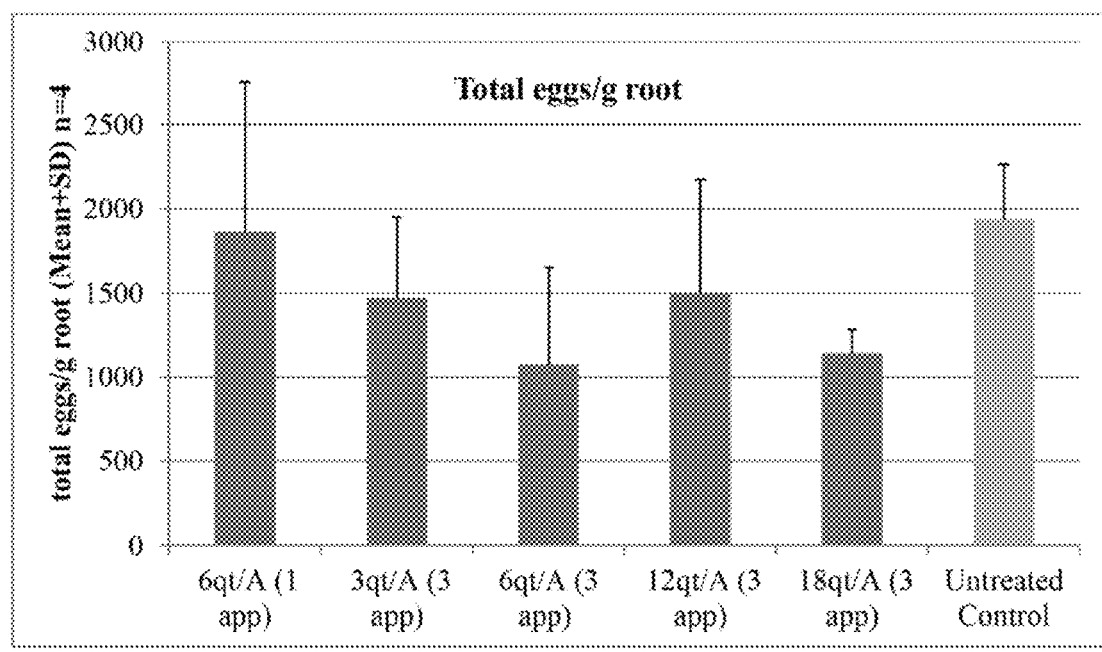
Figure 7C:
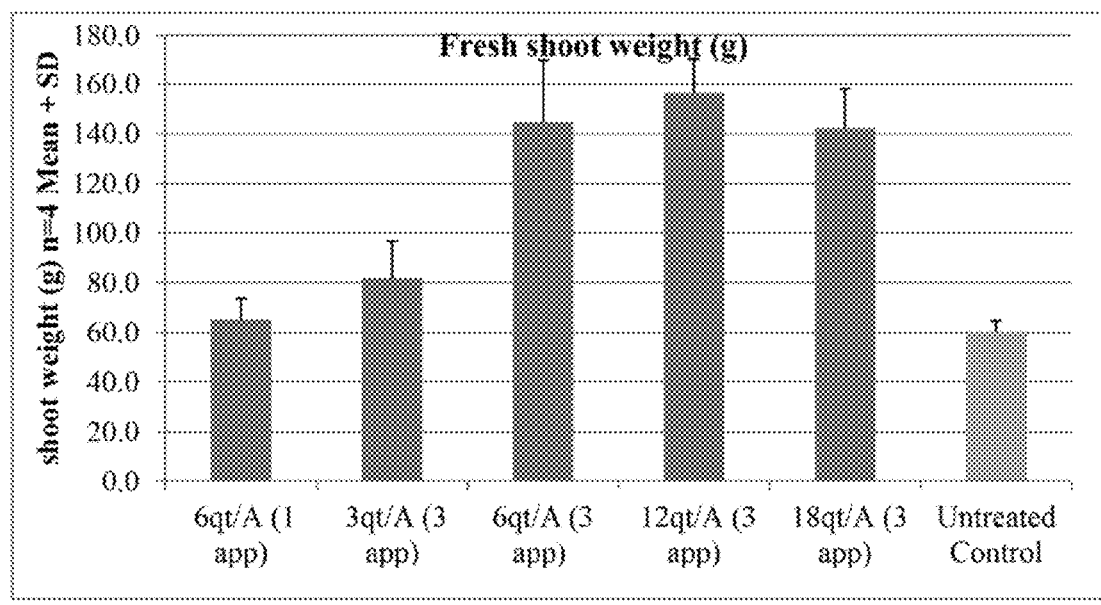

The SERENADE® ASO Product Applied at Multiple Times Compared to One-Time Application The SERENADE® ASO product was applied to tomato plants at transplant into pots having a diameter of about eight inches and every two weeks (i.e., biweekly) thereafter for treatments with multiple applications as detailed in Table 3. The SERENADE® ASO product was applied to the soil around the base of the plant, within about 2 to 3 inches of the base of the plant. A dosage of 6 qt/A is roughly equivalent to 1×10⁵ CFU/g soil (i.e., the soil within two to three inches from the base of the plant). Pots were then kept in a greenhouse for ten days before being inoculated with 1000 root-knot nematode J2 larvae per pot. The plants were harvested 42 days after nematode inoculation, and the galls were rated (see FIG. 7A) and total eggs counted (see FIG. 7B) as described in Examples 1 and 2. The fresh shoots were also weighed to identify the effects of the treatments on plant growth (see FIG. 7C). All data points represent the mean of 4 measurements. Multiple applications of the SERENADE® ASO product generally enhanced nematode control and corresponding plant growth as compared to a single application.

TABLE 3

| Treatment | Dosage | Application |
|---|---|---|
| SERENADE ® ASO | 6 qt/A | At transplant |
| SERENADE ® ASO | 3 qt/A | 3 applications at biweekly intervals |
| SERENADE ® ASO | 6 qt/A | 3 applications at biweekly intervals |
| SERENADE ® ASO | 12 qt/A | 3 applications at biweekly intervals |
| SERENADE ® ASO | 18 qt/A | 3 applications at biweekly intervals |
| Untreated Control | None | None |

Example 6

The SERENADE® ASO Product Applied Once at Transplant at Various Dosages

The SERENADE® ASO product was applied to tomato plants in pots at transplant at various dosages as detailed in Table 4.

TABLE 4

| Treatment | Dosage | Application |
|---|---|---|
| SERENADE ® ASO | 4 qt/A | At transplant |
| SERENADE ® ASO | 20 qt/A (5x) | At transplant |
| SERENADE ® ASO | 40 qt/A (10x) | At transplant |
| SERENADE ® ASO | 80 qt/A (20x) | At transplant |
| SERENADE ® ASO | 160 qt/A (40x) | At transplant |
| Untreated Control | None | None |

Figure 8:
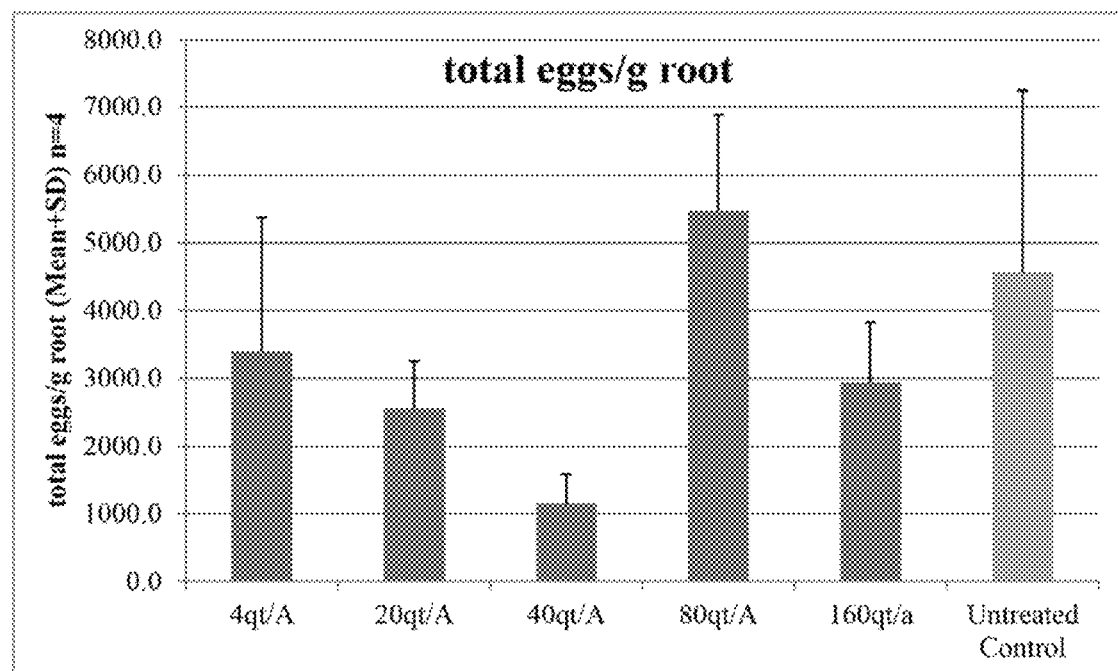
FIG. 8 represents total eggs per gram of root for plants treated with a single application of the SERENADE® ASO product at various dosages.

As noted above, a dosage of 6 qt/A is roughly equivalent to 1×10⁵ CFU/g soil. Pots were then kept in a greenhouse for ten days before being inoculated with 3000 root-knot nematode eggs per pot. The plants were harvested 7 weeks after nematode inoculation and the total eggs counted (see FIG. 8). All data points represent the mean of 4 measurements. Generally, rates that are greater than 4 qt/A resulted in increased control of nematode egg production with the 40 qt/A treatment resulting in about 70% control as compared to the untreated group of plants.

We claim:

1. A method for controlling nematodes in a plant, the method comprising:
    a) identifying that the plant and/or locus for plant growth needs treatment for nematode control; and
    b) applying to the plant and/or locus for plant growth an effective amount of *Bacillus subtilis* QST713 having NRRL Accession No. B-21661 or a mutant thereof to control nematode growth,
wherein the nematodes are selected from the group consisting of *Paratylenchus* spp., *Paratrichodorus* spp., *Criconemella* spp., *Helicotylenchus* spp., *Meloidogyne* spp., *Criconemoides* spp., *Helicotylenchus pseudorobustus* (Spiral HP) and *Helicotylenchus digonicus* (Spiral HD).

2. The method of claim 1 wherein the identifying comprises determining that the locus for plant growth exceeds the economic threshold for nematode infestation.

3. The method of claim 1 comprising applying an effective amount of *Bacillus subtilis* QST713 or a mutant thereof to soil prior to planting and/or at planting.

4. The method of claim 3 wherein the *Bacillus subtilis* QST713 or a mutant thereof is applied at a rate of about $2\times10^{12}$ to about $6\times10^{13}$ cfu per acre for soil drench treatments or $6\times10^{10}$ to about $4\times10^{12}$ cfu per 1000 row feet for in furrow treatments.

5. The method of claim 4 wherein the rate is about $1\times10^{13}$ to about $6\times10^{13}$ cfu per acre or about $7.5\times10^{11}$ to about $4\times10^{12}$ cfu per 1000 row feet.

6. The method of claim 3 wherein the *Bacillus subtilis* QST713 or a mutant thereof is applied to the soil in contact with plant roots or soil at a base of a plant.

7. The method of claim 6 wherein the *Bacillus subtilis* QST713 or a mutant thereof is applied as a single application at a rate of about $7\times10^5$ to about $1\times10^7$ cfu per gram of soil.

8. The method of claim 4 wherein the *Bacillus subtilis* QST713 or a mutant thereof is applied in multiple applications at a rate of about $2\times10^{12}$ to about $6\times10^{13}$ cfu per acre for soil drench treatments per application.

9. The method of claim 1 wherein the *Bacillus subtilis* QST713 or a mutant thereof is applied in multiple applications at intervals of from about 10 to about 18 days.

10. The method of claim 9 wherein the multiple applications are made at a rate of about $1\times10^5$ to about $3\times10^6$ cfu per gram of soil per application.

11. The method of claim 1 wherein the *Bacillus subtilis* QST713 or a mutant thereof is applied to seed.

12. The method of claim 1 wherein the *Bacillus subtilis* QST713 or a mutant thereof is a fermentation product.

13. The method of claim 12 wherein the fermentation product comprises *Bacillus subtilis* QST713 cells or cells of a mutant of *Bacillus subtilis* QST713, metabolites and residual fermentation broth.

14. The method of claim 1 further comprising applying a second nematicide.

15. The method of claim 14 wherein the second nematicide is a chemical nematicide selected from the group consisting of a carbamate and an organophosphate.

16. The method of claim 14 wherein the second nematicide is a biological nematicide.

17. The method of claim 14 wherein the second nematicide is applied at a rate that is less than the rate recommended on a product label for the second nematicide were the second nematicide applied as a stand-alone treatment.

18. The method of claim 14 wherein the *Bacillus subtilis* QST713 or mutant thereof and the second nematicide are applied prior to planting and/or at the time of planting.

* * * * *